United States Patent [19]

Ciervo

[11] Patent Number: 5,507,738
[45] Date of Patent: Apr. 16, 1996

[54] ULTRASONIC VASCULAR SURGICAL SYSTEM

[75] Inventor: Donald J. Ciervo, Merrick, N.Y.

[73] Assignee: Microsonic Engineering Devices Company, Inc., Merrick, N.Y.

[21] Appl. No.: 218,821

[22] Filed: Aug. 5, 1994

[51] Int. Cl.⁶ .................................................. A61B 17/32
[52] U.S. Cl. ......................... 606/1; 604/22; 128/662.03; 128/662.06
[58] Field of Search ............................... 606/1, 169–171; 604/21, 22, 52; 601/2; 128/660.01, 662.03, 662.05, 662.06

[56] References Cited

U.S. PATENT DOCUMENTS

| | | | |
|---|---|---|---|
| 4,920,954 | 5/1990 | Alliger . | |
| 4,922,902 | 5/1990 | Wuchinich et al. | 604/22 |
| 5,069,664 | 12/1991 | Guess et al. | 604/22 |
| 5,312,328 | 5/1994 | Nita et al. | 604/22 |
| 5,417,672 | 5/1995 | Nita et al. | 606/169 |

*Primary Examiner*—Stephen C. Pellegrino
*Assistant Examiner*—Michael Peffley
*Attorney, Agent, or Firm*—Charles E. Baxley

[57] ABSTRACT

An ultrasonic vascular surgical system for passing by an artery lesion having a restricted passageway. The system includes a generator, a handpiece having a velocity transformer, a coupling unit having an inner transformer portion with a groove formed by opposite groove sidewalls and having an outer cylindrical cap portion for compressing the groove sidewalls and groove and a guide wire with an end disposed in the groove and gripped by the groove sidewalls.

10 Claims, 3 Drawing Sheets

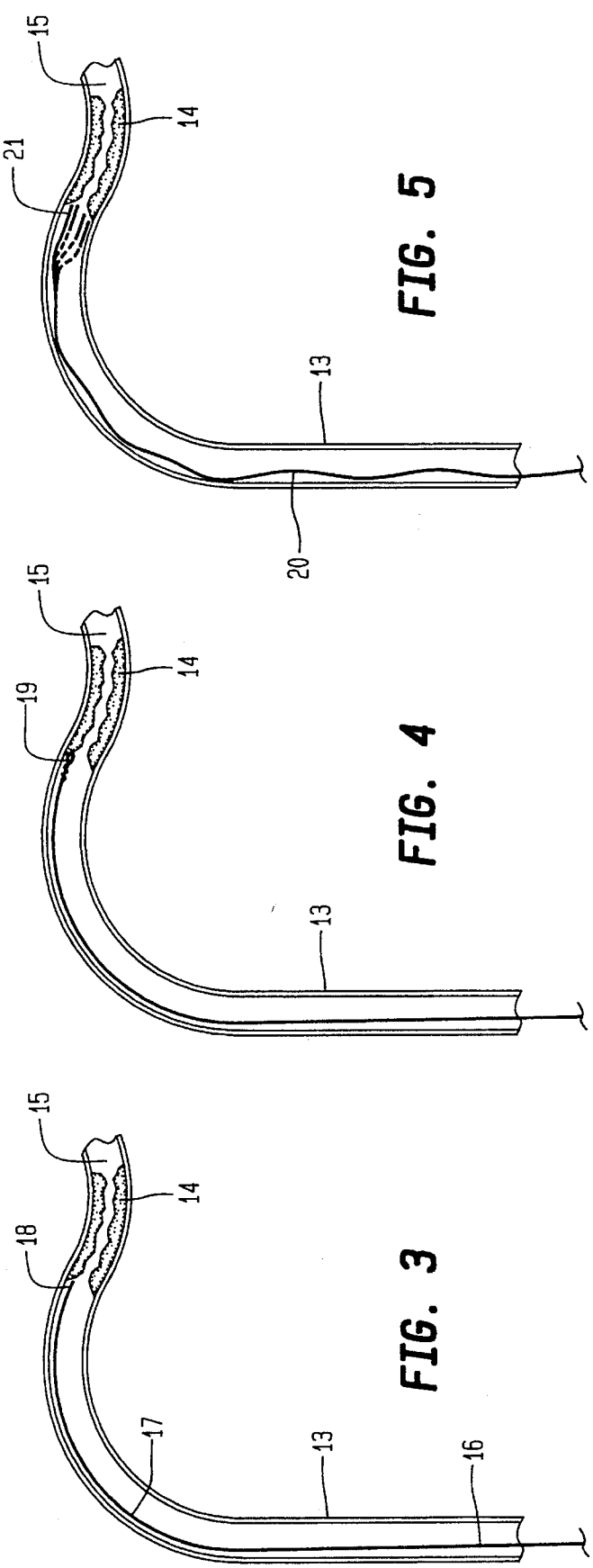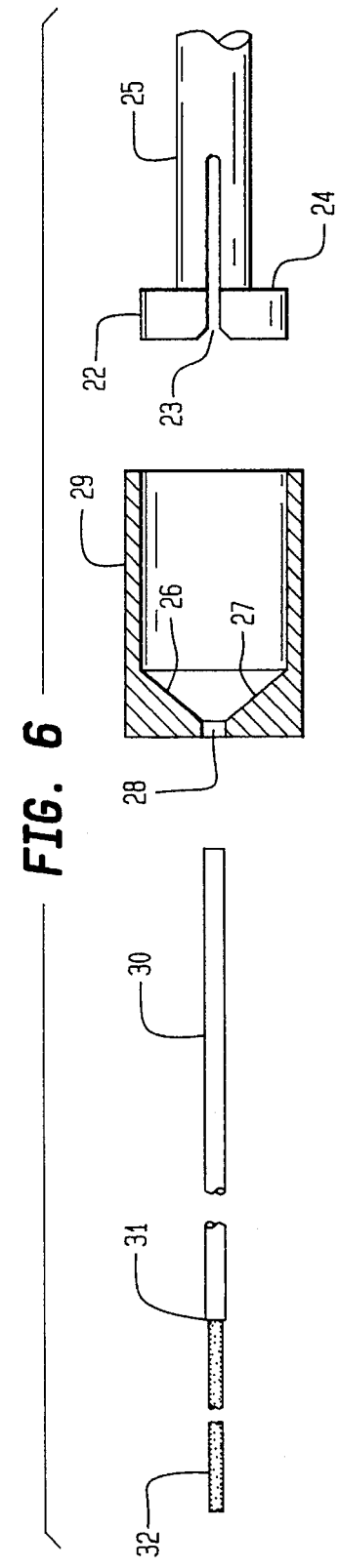

ULTRASONIC VASCULAR SURGICAL SYSTEM

BACKGROUND OF THE INVENTION

1. Field of the Invention

This invention relates to an ultrasonic vascular surgical system, and more particularly to an ultrasonic surgical system having a low frequency velocity transformer that is provided with a coupling unit with an untuned guide wire.

2. Description of the Prior Art

One prior art ultrasonic surgical system is described in U.S. Pat. No. 4,920,954 which issued on May 1, 1990. In that system, a generator has a lead for connection to a power supply with a handpiece having a lead connected to the generator. A velocity transformer is driven by the generator and has a vibration end portion with a guide wire having an inboard end connected fixedly to the vibratory end portions.

Another system is described in U.S. Pat. No. 4,920,954 as having a metal, composite guide wire comprised of a plurality of long thin wires of platinum, titanium and other exotic alloys which are combined to form the composite guide wire. This type of multi-alloy composite guide wire is used extensively in CAT labs for reaching remote areas in the human body, typically a lesion within an artery or vessel. Although insertion of this composite guide wire requires a skilled professional who has the ability to maneuver the tiny composite guide wire through a maze of channels and branches, the insertion of the composite guide wire can at times lead to difficulties that and therefore increase the risk of exposure to harmful x-rays to both patient and professional during angioplasty procedures. An attempt to speed up this operation can hamper ability of a surgeon and/or a practitioner.

Another system employs a different type of guide wire which is formed in increments to control change its bending characteristics, providing a means for protecting the vessel from perforation through increased flexibility of the wire. These increments are metal and are bonded usually by electron beam welding of dissimilar materials, or through brazing, to combine different bending characteristics. The tip of such a guide wire is usually composed of a central core of wire alloy, and around it as fine hair-like wire is spun, forming a soft spring located at the tip of the guide wire. This spring-like tip is as soft as a sponge and buckles easily through its own weight thereby providing rapid, easy passage through some of the most intricate of curves within the human body.

When one of the aforementioned guide wires is used in angioplasty procedures, it is introduced into a blood vessel via an introducer. The wire becomes almost life-like as each centimeter of it is pushed through the introducer and into the vessel. It makes its way toward a branch or another final destination (possibly a partial obstruction or any other biological malformation needing to be reached for diagnosis). It may be possible when manipulating the guide wire, due to necessary twisting and shoving, for an incorrect channel to be reached. Perhaps the wire may get jammed into a tight obstruction where the tip can actually buckle and can appear like a knot under fluoroscopic conditions. Any attempt to release the tension of the wire may in fact cause damage to the fine coil of wire which allows the tip to contact fragile blood vessels.

A further prior art system has a guide wire which is a heat-sensitive composite guide wire, where the guide wire is formed with several different metals combined in a manner that such wire material is formed as a semicircle or other portion of a circle, and combined axially to complete a full circular cross section. Each section of the wire is adhered together to permanently construct a straight member at room temperature. If heat is applied to different segments along the length of such a guide wire, the heating will cause bending of the wire due to the different coefficient of expansion of each of the materials bonded. By controlling the duration and the amount of energy applied to the composite guide, different bending angles may be acquired. Cooling the composite guide wire will cause the guide wire to bend in the opposite direction, allowing multi-curvature lumens to be entered. To combine a multi-temperature guide wire system that not only bends in one direction from its equilibrium position at room temperature and in the complete opposite position when cooled, seems to implant a greater degree of difficulty to the practicing CAT specialist.

Yet another prior art system has a guide wire which provides a unidirectional temperature change. Such a guide wire has a single heating element which is fabricated into the abovedescribed composite guide wire with little difficulty. Such a wire still maintains the flexibility and small cross sectional area needed to cross tight lesions. The heating element may include pieces of nichrome wire imbedded into the guide wire, with one length insulated from the other but both extending from one end to the other; or it can include a single strand of nichrome wire with the strand being insulated from the guide, along its total length, but attached to the far end of the guide making a complete path reaching to the near end for power control bending. Application of a small current through the nichrome wire will cause heating of the composite guide wire system which in turn will cause the dissimilar metals to bend in a selective direction. Controlling the current can cause precise bending of the guide wire, allowing one to easily manipulate the wire as it is inserted through the vessel. To change directions, this prior art guide wire can be twisted through all angle of 180 degrees or any other fraction thereof for redirecting such guide wire into a new channel within the arteries. Although such a guide wire is not slippery, it can be directed through a vessel, though resistance to the user can be a problem when a significant amount of wire remains within the arteries, possibly increasing the total time and the complexity of standard guide wire procedures.

In some cases, the prior art guide wires become resistant as they are pushed through a vessel. This can be caused by the wire passing some form of a lesion which could reduce the actual lumen of the vessel by up to 90% or conceivably block it completely. When the wire is first inserted the resistance is low but as more wire enters the vessel, there is increased contact with the inner lumen of the vessel thereby increasing the resistance. As the wire approaches blood vessel curvatures, the guide wire takes on a mind of its own. The wire's natural tendency is to stay straight in the arterial lumen. This causes the wire to ride along the outer circumference of the vessel wall while passing through it, in an attempt to find the path with the least amount of resistance. Resistance is increased because the wire has a tendency to remain straight and vessels curve. The tighter the curvature of the lumen, the more resistant the wire becomes. Surface area along the length of the guide wire increases as the wire inches forward. More than 50 centimeters into the lumen a guide wire may become noticeably more difficult to direct and passage to an occluded segment within the vessel could in some instances take a few hours, or possibly even longer, depending upon the skill or luck of the specialist.

To overcome the resistance of guide wire direction, the prior art guide wire as used may be coated with a gel or possibly coated with a Teflon-like material. These substances may decrease the total resistance of the wire. It is also possible to coat the wire with a selective genetic substance that will react with the metal composition of the wire and the inner walls of the vessel.

Coatings like the genetic or gel substances may need to be replaced several times before the wire reaches its designated site, possibly increasing the risk to the patient. Teflon materials seem to be safe when placed in the body but might not achieve total or near total reduction of wire resistance. In addition, the probability of crossing a high grade occlusion does not necessarily increase either with or without slippery coatings placed on the wire.

Still another prior art system has a guide wire with a small motor or a pnuematic device for spinning the guide wire at a significant speed. The resistance of the wire is reduced and passage of the wire through lesions is facilitated. The guide wire can also dissipate or redirect heat energy along some of the tight curves within the vessel. Heat energy applied to one particular area within the vessel can cause the guide wire to easily perforate the delicate structure of the vessel wall. In addition, the end of the guide wire has a tendency to twist and knot like a rubber band, when overly twisted, thus causing the guide wire to jam or fracture within the arterial lumen. To overcome the tangling effect of rotating devices, the guide wire is designed in a way that increases the resilience of the wire, but in turn removes the softness of the tip. These properties designed into this prior art guide wire have the problem that they increase the chance that the guide wire will drill through the vessel wall.

Another problem with this guide wire is that the wire, when spun, causes the blood to coagulate around the wire forming clots within the vessel, possibly causing cardiopulmonary damage. Clot-reducing agents, as heparin, can be used to reduce blood clotting with rotational devices, but the effect of centrifuging the blood can occur. It is possible that localize whirlpools are generated with such a spinning guide wire in the cardiovascular system. Passage, with the help of such a device seems to cause unnoticeable long term damage to the vessel, which could be the site of newly formed stenosis.

SUMMARY OF THE INVENTION

The problems of the prior art systems and respective guide wires which include, specifically, the increased resistance due to natural bending within the vessels resistance caused by high surface area contact along the inner walls of vessels and crossing past a high grade lesion are overcome by the system and guide wire according to the present invention. Unlike most prior art guide wire systems that attempt to decrease resistance by spinning the wire, coating with slippery substances or heating the mechanism, the device according to the present invention actually eliminates the necessity of such measures, by providing a system and guide wire which transmits a low frequency ultrasound into the end of the guide wire, and thereby avoids such problems.

Such low frequency vibration alone cannot excite the wire. The guide wire of the present invention has a long length, and a soft tip. These features do not provide an ideal situation exciting the guide wire with waves at a relatively constant frequency. The guide wire has a length of about 60 to 70 inches (150 to 180 cm.) and a diameter of about 0.010–0.035 inches and is untuned for the transducer and power supply and these factors, contribute to significant losses in the guide wire. The waves traveling through the guide wire are attenuate, thus reducing the vibration needed for slipperiness.

This low frequency vibration system of the present invention is unlike most prior art ultrasonic systems. In the prior art systems, the guide wire is actually tuned to a length equal to multiples of half wavelengths, to vibrate at a discrete frequency, and to keep the prior art guide wire in tune or impedance matched with the prior art ultrasonic generator or audio amplifier which typically drive the prior art transducer near or at the frequency which gives the most efficient point of operation. The prior art transducers varying load and power levels are constantly monitored by an electronic circuit which makes the necessary adjustments such that the optimum conversion of electrical energy input to mechanical displacement output is achieved for the destruction or obliteration of plaque, the fragmentation of stones or perhaps the removal of a cataract called phacoemulsification.

It is desirable to avoid the high cost of fine tuning a guide wire that meets the criteria for ultrasonic wave propagation, like solid wires of high strength steel or exotic alloys with very low dampening. The guide wire of the present invention is a composite guide wire which initially is not designed with ultrasonic in mind, as a means of guide wire delivery. The guide wire of the present invention has a spring-like tip and a multi-alloy composition, and exhibits such a high degree of sound absorption that it presents the challenge of not only attaching the wire to the ultrasound source with the least amount of energy loss, but it also presents the challenge of how to best drive the wire in order to get the proper amount of uniform slipperiness needed for angioplasty procedures. For this purpose, the guide wire of the present invention has a selective coupling unit or attachment device or pressure cap.

The wire system of the present invention can excite the multi-composition guide wire of long or short length, without the need of tuning or combining the wire to a screwable tip or sonic velocity transformer by gluing, brazing, soldering, threading or welding prior to application of sonic energy. The guide wire performs this operation by a unique coupling unit or attachment device or integrated tip design, which is part of the velocity transformer that accepts the guide wire. This coupling unit insures a single use only, thereby preventing the spread of contagious diseases from contaminated instruments. Most importantly, the coupling unit provides a high degree of mechanical coupling for the transmission of sonic energy without the need of specialized tip attachments on the velocity transformer so often used in the typical ultrasonic generating equipment.

Sonic energy is delivered from the velocity transformer, through the coupling unit to the guide wire by actually banging the end of the wire like a jack hammer. This jack hammer action is produced by modulating the frequency of the transducer within a specified operating window. Within that window the transducer's changing frequency travels down the length of the wire, similar to a solid bar partially dampened at one end and free at the other end. Each wave at the coupling unit or tip/wire attachment is changing for each cycle that is put into the guide wire. The wave moves along the length of the guide wire and upon reaching approximately ¾ of the total length of the guide wire, due to the nature of the guide wire, it begins to vibrate more transversely, gradually increasing in amplitude and whipping the tip erratically. At the spring like junction of the guide wire, the waves transfers from partially longitudinal to a more transverse wave propagation similar to a string or cord loose at one end of a room, and at the other end, one can whip the cord causing waves to migrate through the cord.

The transverse wave which rides along the spring formed portion of the guide wire causes the very tip of the guide wire to chatter in different directions with varying amplitude. The erraticness of the guide wire tip whipping in many directions increases the probability of passing the guide wire through high grade occluded lesions within a vessel, which for the most part is quite difficult for prior art guide wire delivery systems and especially, the conventional delivery of guide wires by hand.

Preventing waves from superimposing at different frequencies cause the guide wire to vibrate with a uniform slipperiness without discrete points of movement and no movement usually caused by standing waves when operated at a constant frequency. For the present invention, the wire is being banged over a range of drive frequencies. Attachment to the sonic velocity transformer is no longer a threat to the wire of the present invention when the wire is slightly over driven and begins to vibrate in a transverse mode of vibration. This typically happens for unprotected prior art wires smaller than 0.060 inches in diameter, especially prior art wires around 0.020 inches that have a natural tendency to initially vibrate transversely as the smaller wires collapse easily just by its own weight or when longitudinal waves veer slightly off from the center of the velocity transformer axis bending or throwing the wire from one side to the other setting up a pattern of waves which rapidly increase in amplitude. These properties of the prior art wires ultimately fatigue the attachment to the tip of the velocity transformer, like that of a paper clip held between ones fingers and bent back and forth until heating and microscopic cracks make its way through the metal, thus reducing the total cross sectional area that keeps the metal intact.

Unprotected prior art wires, which suddenly transform into transverse vibrating elements contain nodes at the point of attachment to velocity transformers. The problem of runaway wires was overcome by placing a close fitting sleeve over the prior art wire and up to the velocity transformer. These sleeves attenuate the transverse whipping of the wire and eliminate the possibility of a node forming at the attachment. They also increase the working diameter of the wire, making it more difficult to enter small vessels. A close fitting protective sleeve, made to limit or dampen the whipping of the wire, is not necessarily for this invention. Other protective attachments that lessen the transverse whipping or keep the wire ridged at the point of attachment to the velocity transformer are also not required for the present invention, thereby eliminating the need of over complication in the set up procedure. The uniform slipperiness of the guide wire of the present invention helps considerably when performing guide wire techniques since there is no discrete nodes and anti-nodes (loops) along the length of the wire encountered with standing wave devices operated at a constant frequency. At a constant frequency, the nodes and loops along the prior art wire come in contact with the inner walls of a vessel or perhaps in some cases a catheter. The nodes (points of no movement) are actually points along the prior art wire where a maximum amount of stress and strain occur which creates an energy concentrating point that leads to heating of the wire at stressful amplitudes to the point that the vessel can be damaged from over exposure to heat. The loops in the prior art wire system produces heat not by stresses in the wire, but by frictional contact between the wire and inner vessel wall, and by cavitation of liquids that acoustically couple sonic energy to nearby tissue. For example, cavitational coupling of energy can be felt ill ultrasonic cleaning tanks which have a low power per area density and in sonic liquid processors or cell disruptors which have a more destructive power per area energy density, each directing heat along inner vessel walls. Changes occur within the metallurgical state of the prior art wire changing its material characteristics, such as the modules of elasticity, velocity of sound,and the fatigue strength of the material. The node high frictional area, which is theoretically located midway between the ends of a free ended bar intended to vibrate at half wave fundamental frequency, impedes the ability of the wire which has many nodes and loops along its length from actually progressing through the vessel with the least amount of effort by the practitioner. In the standing wave wire, contact area away from the node, and progressing to a loop, becomes more and more slippery but in a non-linear fashion directing acoustic energy into a vessel wall or surrounding tissue, especially when the vessel becomes curved and more energy is delivered to that area. Addition of fluid, for cooling purposes, in an attempt to cool the wire, if the lumen is large, greatly limits the size of the vessel which may be entered.

The system of the present invention alleviates these difficulties encountered with prior art vibrating apparatus and provides a simple safe and novel method of generating and directing ultrasonic energy into an untuned guide wire which greatly reduces time and effort for crossing high grade lesions.

These and other objects and many of the attendant advantages of this invention will be readily appreciated as the same becomes better understood by reference to the following detailed description when considered in connection with the accompanying drawings in which:

BRIEF DESCRIPTION OF THE DRAWINGS

FIG. 3 is a sectional view of an artery containing a distal end section of a guide wire the ultrasonic surgical system of FIG. 1;

FIG. 4 is a sectional view corresponding to the sectional view of FIG. 3, and having a knotted guide wire distal end section;

FIG. 5 s a sectional view corresponding to the sectional view of FIG. 3 and having a vibrating guide wire distal end section;

FIG. 6 is an exploded sectional view of a coupling unit of the guide wire of the system of FIG. 1;

DESCRIPTION OF THE PREFERRED EMBODIMENT

Figure 1:
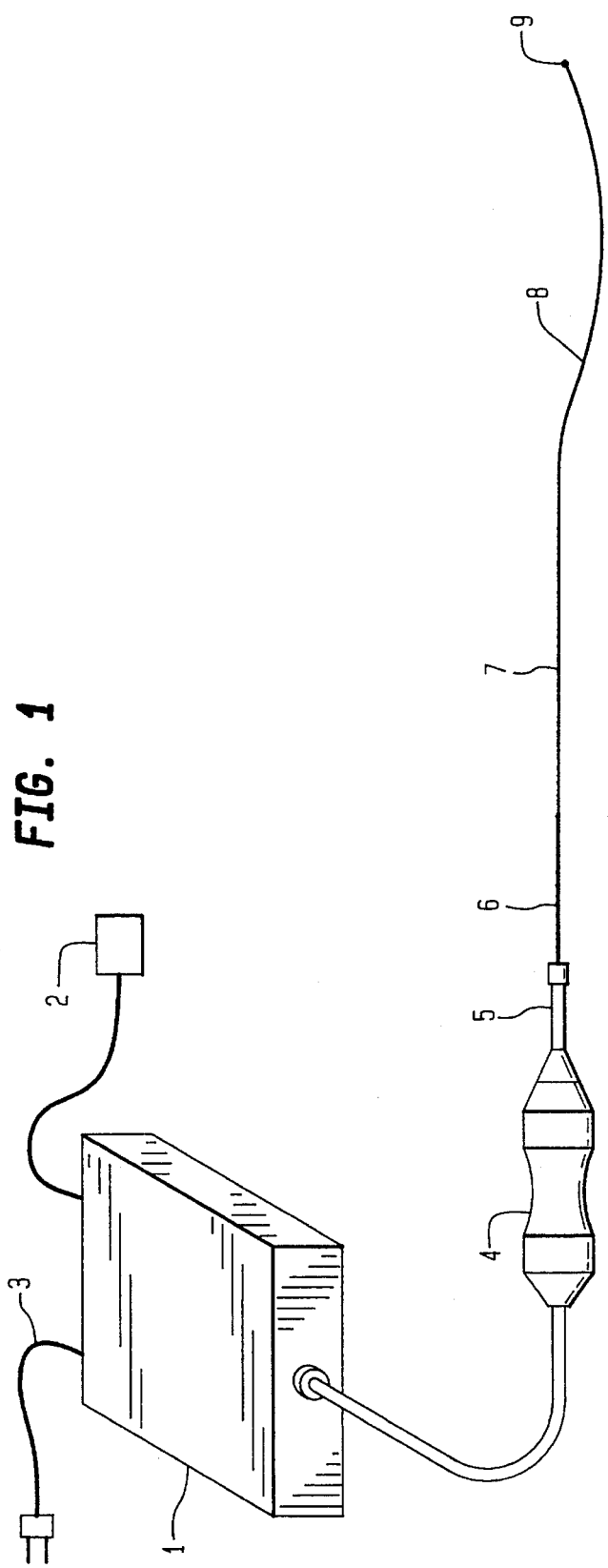
FIG. 1 is a perspective view of an ultrasonic surgical system according to the present invention.

Referring now to the drawings wherein like reference characters designate like or corresponding parts throughout, there is illustrated in FIG. 1, an assembly or device or ultrasonic surgical system generally designated as reference numeral 50 which includes a generator 1, having a foot-switch 2, a standard plug 3, a handpiece 4, a transducer 5, a coupling unit 29 and a guide wire 16. The guide wire 16 has an inboard guide section 6, an intermediate guide section 7, an outboard guide section 8 and a proximal or distal end section 9.

Figure 2:
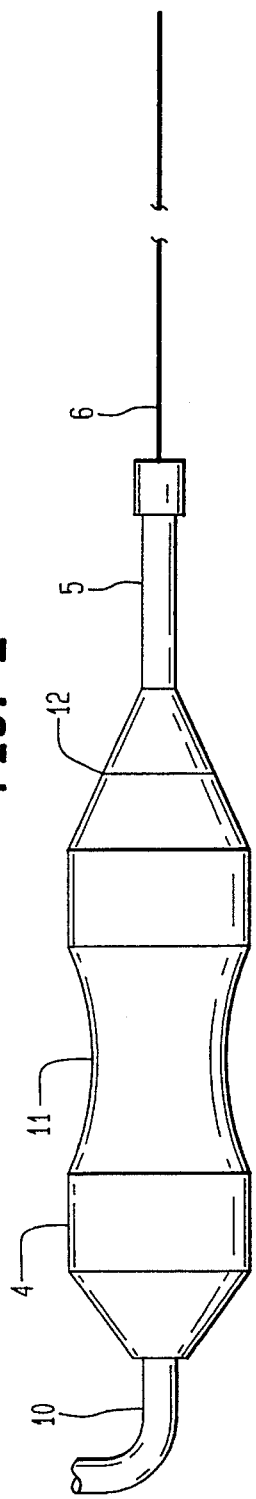
FIG. 2 is all enlarged view of a portion of FIG. 1.

As shown in FIG. 2, the handpiece 4 has an electrical cable 10 which connects the generator 1 to a handgrip 11. A juncture portion or juncture point 12 is formed between the handgrip 11 and the transducer 5 which has a coupling unit 29 connected to the inboard guide section 6.

As shown in FIG. 3, the guide wire 16 is positioned inside a vessel or artery 13. The vessel 13 has a plaque or plaque deposit 14. The plaque deposit 14 has a passageway or lumen 15 which extends therethrough. The guide wire 16 passes through a curved portion 17 of the vessel 13. The plaque deposit 14 has a blockage portion 18 at an end thereof, where the guide wire 16 is blocked. As shown in FIG. 4, the blockage 18 causes a bend portion or knotted portion 19 at the distal end section 9 of the guide wire 16.

As shown in FIG. 5, the guide wire 16 has a rippling effect or series of waves 20, which cause a nonuniform motion or a transverse travel 21 of the guide wire distal end section 9. The transverse travel 21 helps to direct the distal end section 9 through the lumen 15 of the plaque deposit 14.

As shown in FIG. 6, the coupling unit 29 has a velocity transformer 25, with a plurality of exterior axial splines or teeth or riblets 22, a transverse groove or slot 23 and a breaking step 24. The coupling 29 also includes a pressure cap 30 having a cylindrical wall 26, an angle portion or end wall 27, and a through hole 28 through the end wall 27. The transformer 25 forms an inner coupling portion and the pressure cap 30 forms an outer coupling portion. The outboard wire section 9 has a wire junction 31 and a tip wire portion 32 which is more flexible than rest of the wire section 9 in order to permit passing of the tip portion 32 through the lumen 15.

Figure 7:
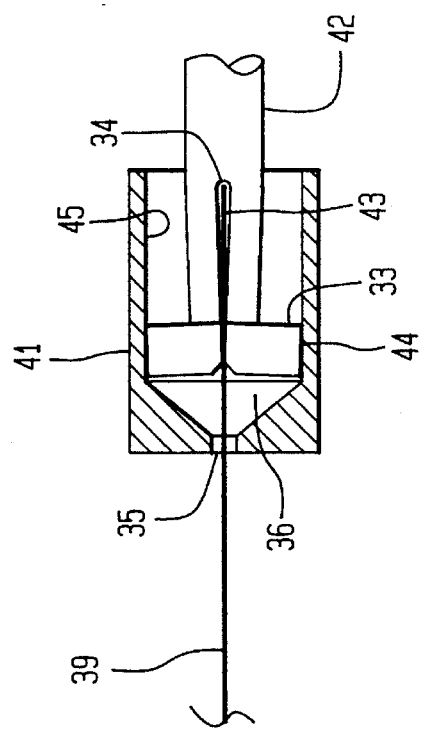
FIG. 7 is a sectional view of the coupling unit of FIG. 6 before fusion of the parts thereof.

As shown in FIG. 7, which is a sectional view of the coupling unit 29 before fusion of the velocity transformer 25 to the pressure cap 30, the riblets 22 have respective contact areas which form a total contact area 33, and frictionally engage the cylindrical wall 26 and its radial inner surface. The slot 23 in the velocity transformer 25 has a bottom portion 34. The hole 28 in the pressure cap 30, opens into a stress relieving void or space 36 for relieving the guide wire 16 during vibration.

Figure 8:
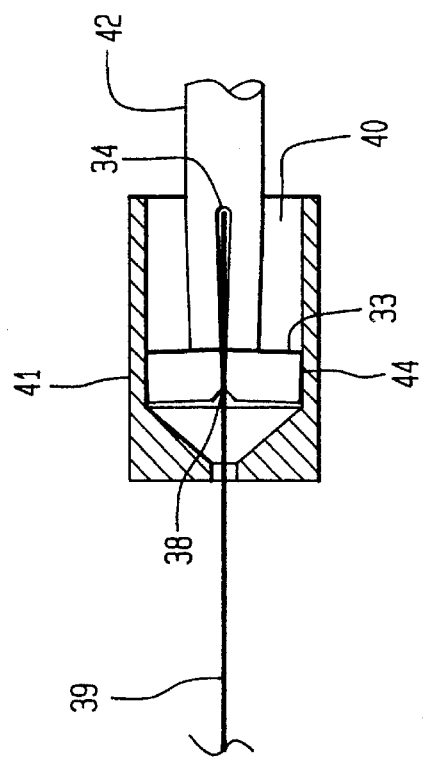
FIG. 8 is a sectional view of the coupling unit of FIG. 7 after fusion of the parts thereof.

As shown in FIG. 8, which is a sectional view of the coupling unit 29 after fusion of the velocity transformer 25 to the pressure cap 30, a region 37 of fusion and of high frictional movement is formed. The slot 23 also has a true loop portion 38 which grips the wire section 6 of the guide wire 16. The wall 26 of the pressure cap 30 and the velocity transformer 25 have a void or cavity 40 therebetween. In this manner, the pressure cap 30 is locked to the transformer 25, and the guide wire 16 is gripped by the velocity transformer 25. The loop portion 38 around the slot 23 have opposite resilient slot sidewalls, which are compressed by the pressure cap 30, for gripping the guide wire 16.

In operation, as shown in FIG. 1, the generator 1, which derives its energy through the plug 3, converts 110/120 electrical AC signal to electrical energy within the ultrasonic spectrum, in the form of a "hammer-like" signal to the handpiece 4, each time the foot switch 2 is depressed. The handpiece 4 securely locks in the transducer 5, such that forward and backward manipulation along with torque may be applied for directing the guide 16. The "hammer-like" motion makes its way through the guide section 6, which is a section of the guide 16 in the form of longitudinal motion. The guide section 6 is comprised of a material which has a relatively high modules of elasticity to keep the guide wire 16 stiff when directing it through the artery or vessel 13. A portion of the guide wire section 7 which is also a section of the guide wire 16 is a bit more flexible than the area of the guide wire section 6 for advancing the guide 16 through the tortuous curves within the the lumen 15. Along the sections 6 and 7 the, guide wire 16 remains slippery and can be felt with ones hand to be smooth and continuous from the sonic energy applied to the system each time the footswitch 2 is depressed. As the longitudinal wave travels through the guides sections 6 and 7, discrete nodes and loops are not present due to the "hammer-like" way the proximal end of the wire 16 is being energized, creating a uniform slipperiness along the wire 16 which decreases the total resistance within the vessel lumen during procedures. When the longitudinal wave reaches the portion of the wire labeled 8, the wave converts into a transverse wave with little or no reflected wave propagating back into the sections 6 and 7 which would begin a standing wave pattern along the wire with discrete nodes and loops equaling one-half wavelength apart from one another, deteriorating the uniform slipperiness needed for this application. The transverse wave is similar to a wave encountered with string instruments, ripples that guide the spring like portion 8 thereby reducing contact area along the vessel lumen 15 and whips the guide distal end 9 vigorously with no discrete amplitude or direction, thereby increasing the probability that large or tight lesions may be crossed or bypassed by unskilled CAT specialists. Energy supplied to the wire from the transducer 5 is far below the densities achieved from prior art cavitational devices typically developed for the destruction of kidney or gall stones and devices that obliterate plaque within the human artery. The energy directed from the guide portions 6, 7, 8 and 9 does not threaten delicate vessels from direct heat or the making and breaking of bubbles that could conceivably cause damage to these vessels. Thus, this invention provides a mechanical slipperiness which would greatly reduce risk from over-generous manipulation of the guide 16 and reduce the time lapsed from crossing a tight lesion or plaque 14.

Referring to FIG. 2, the transducer hand piece 4 which receives electrical energy from the cable 10, contains elements typically used in ultrasonic applications such as piezoelectric and magnetostrictive type motors which are widely used for this purpose of developing sonic vibration. Application of tailored electrical waveforms is transformed into a mechanical movement by these motors that can be adapted to different loads. Each motor can couple to the velocity transformer 5 which is typically used for the amplification of sonic vibration due to its designed contour. The handpiece grip 11 is shaped in a manner that makes it small in the hand and easy to handle when wet or slippery from solutions that may come in contact therewith during guide wire procedures.

The velocity transducer 5 snaps into the handpiece 4 at the junction 12 which is recoupled from sonic vibration typically by an O-ring, or by quarter wave isolation of the velocity transducer 5 from the case at junction point 12, which could otherwise transmit sonic energy into the handpiece 4, contributing to losses that might otherwise be applied to the guide wire section 6.

FIGS. 3, 4 and 5 show the natural tendency of the guide wire 16 to remain straight within the artery or vessel 13 and follow the path with the least amount of resistance as the guide 16 is inched forward. As illustrated, the vessel curved portion 17 will follow the vessel 13 at the outer most curvature causing the guide 16 to become blocked at the blockage portion 18 so that it cannot pass through the lumen 15 which extends through the plaque 14 within the vessel 13. Further direction typically will cause the guide 16 to form a knot 19, as shown in FIG. 4, like that of a rubberband in the lumen of the vessel 13, just before it can pass through the lumen 15 of the plaque or obstruction 14.

Application of the sonic energy in the form of a "hammer-like" motion to the guide 16, creates the rippling affect 20, shown in FIG. 5, that not only reduces contact area along the vessel wall 13, but whips the tip of the guide in a nonuniform motion 21, such that the lumen 15 disposed in the obstruction 14, can easily be passed. The guide 16 has a greater probability of crossing such a lesion due to the transverse motion 21.

FIG. 6 shows the coupling unit 29, and shows the piece-by-piece assembly of the wire section 6, the pressure cap 30, and the velocity transformer 25, needed for instantaneous coupling of sonic energy into a wire without the need of gluing, brazing, screwing or other specialized methods requiring tools. The guide 16 has an inboard wire section 6 which is directed into the centralized through the hole 28, which is primarily needed for centering the wire section 6, into the sonic velocity transformer tip 25, through a slot 23 molded or cut into the end of the velocity transformer 25. The pressure cap 30 is pressed over the sonic velocity transformer 25 after the wire has been secured into the slot 23. As the pressure cap 30 is pressed over the velocity transformer 25, the inner walls 26 of the pressure cap 30, make contact with riblets 22, of the velocity transformer 25. The riblets 22 are placed into the loop of the velocity transformer 25 and are actually small grooves creating peaks and valleys that will eventually melt and bond to the inner wall 26, of the pressure cap 30. The contact area is reduced along the inner wall 26, of the pressure cap 30, by the peaks of the riblets 22, for the purpose of creating friction along the riblets 22 and the inner wall of the pressure cap 30, which is needed for welding the pressure cap 30 to the velocity transformer 25 after a short burst of energy is applied to the system. The pressure cap 30 will remain as an integral part of the velocity transformer 25 with a smaller gap remaining along most of the inner wall 26 of the pressure cap 30 just after the breaking step 24 in the velocity transformer 25. The velocity transformer 25 integrated with the pressure cap 30 will have a slightly lower operating frequency, due to the increased mass loading of the pressure cap 30. The velocity transformer 25 will also exhibit a slight shifting of the true nodes along its length toward the increase mass loading contributed by the pressure cap 30. The breaking step 24 is required to limit contact area to a small segment at the true loop of the velocity transformer 25, which contain the riblets 22 for purposes of significantly reducing attenuation of the velocity transformer 25 by the inner wall 26 and mass of pressure cap 30, required to weld the pressure cap 30 to the velocity transformer 25.

Angle portion 27 has the purpose of stress relieving its attachment to the wire section 6 which is secured into the slot 23. The pressure cap 30 is firmly pressed over the velocity transformer 25, and after the application of a short burst of sonic movement, a permanent weld is fused therebetween.

When "hammer-like" waves propagate into the wire section 6, after fusing the pressure cap 30 to velocity transformer 25, no heat is concentrated at the tip of the velocity transformer 25, due to the efficient couple means 29 presented with this invention. With the couple means 29, more of the energy can be utilized at the outer tip 32 of the guide wire 16, after its long journey down the guide wire 16, and after passing through the junction 31, that has already contributed to some losses of the wave.

In FIGS. 6, 7 and 8, the guide 16 can be viewed with pressure cap 30 and velocity transformer 25 before and after sonic energy has been applied, during manufacture creating the fusing of riblets 22 to the inner wall 26 of the pressure cap 30. The contact area 33 from the peak riblets 22 remains relatively low prior to activating the sonic source. After initiating the energy, vibration from the velocity transformer 25 causes the riblets 22 to begin to flow with the inner wall 26 of the pressure cap 30 creating the bond needed to combine the pressure cap 30 to the velocity transformer 25.

Keeping the wire section 6 snug in the velocity transformer 25 is a key feature of the present invention and is achieved when the wire section 6 is placed against the bottom portion 34 of the slot 23, thereby keeping the contact area 33 as high as possible along the surrounding wall of the slot 23, without adding losses from dissimilar material contact of the velocity transformer 25 and the wire section 6. The wire section 6 is held in place prior to fusing, by the combination of the central slot 23 pinching the wire section 6 at the true loop portion 38 of the velocity transformer 25, thus keeping the stresses to a minimum and preventing the flow of material, such as plastic, around the wire section 6, during the time energy is applied to the system during fusing. The flow of material, such as plastic about wire section 6 during that instance of fusion relieves the force applied to the wire section 6 by the groove or slot 23 contained within the velocity transformer 25.

The pressure cap 38 having the central through the hole 28 and the stress relieving void 36 are specifically designed to hold the wire section 6 in place during and after application of sonic energy, preventing the wire section 6 from disengaging from the velocity transformer 25 during guide wire attachment procedures. Wire stability is accomplished by the use of the void 36 for centralizing the wire section 6 in the velocity transformer 25 and keeping the wire section 6 within the slot 23 axially within the velocity transformer 25 such that the wire section 6 is prevented from slipping in a transverse mode during the application of sonic energy. In combination with the void 36 contained within the pressure cap 30, a space is provided by the void 36 preventing the wire 9 from bending at the true loop 38 of the velocity transformer 25 throughout the useful life of the wire section 6, thereby avoiding metallurgical damage that might occur to the wire section 6 from excessive bending either from the motion of sonic waves or the handling of the wire section 6, that causes a reduction of the total cross sectional area of the wire section 6, like that of a paper clip overly bent in ones hands. The pressure cap 30 extends beyond the true loop 38 of the velocity transformer 25, creating another void or cavity 40 needed to increase the mass of the pressure cap 30 without overly increasing the diameter of the pressure cap 30 that would accent the ability of exciting other modes of vibration that could otherwise contribute to losses or possibly add the dimension of transverse vibration which would fatigue the wire section 6 or velocity transformer 25 at a point of high stress. The additional mass of the pressure cap 30 aids in the ability of the riblets 22 to fuse to the inner wall 26 of the pressure cap 30 during the fusing stage. The pressure cap 30 being more or less fixed from the additional mass as compared to the motion exhibited from the velocity transformer 25, creating a region of high frictional movement 37 needed to cause the pressure cap 29 and the velocity transformer 25 materials to reach the melting point for fusing to take place.

It should be understood that other applications of this invention include, short wires or tubes which can be used to clean plaque from teeth, removing cataract lens called phacoemulsification, cleaning of small blind holes from contaminants within, injection of viscous fluids through small tubes and other applications which would benefit from the motion exhibited from this invention. This invention also eliminates the need of autoclaving instruments prior to a procedure, reducing time, operating costs and mechanical fatigue encountered from other vibrating devices typically designed from exotic alloys. This disposability of this invention also contributes to its effectiveness of keeping costs down and most importantly reduces the risk to patients from fatal viruses which could be transmitted from contaminated devices. The uniqueness of this invention eliminates the need of tuning attachments, such as other wires or tips, prior to the application of energy and provides a simple and effective means of attaching such tools to this instrument without sacrificing power.

It should be understood that the foregoing relates to a limited number of preferred embodiments of the invention which have been by way of and that it is intended to cover all changes and modifications of the examples of the invention herein chosen for the purpose or the disclosure, which do not constitute departures from the spirit and scope of the invention.

What is claimed:

1. An ultrasonic vascular surgical system comprising:

an ultrasonic generator;

a transducer, with said transducer connected to said ultrasonic generator;

a velocity transformer with said velocity transformer connected to said transducer;

a guide wire having an inboard end, with said inboard end of said guide wire connected to said velocity transformer;

a pressure cap having a inner wall defining a cavity, with said velocity transformer projecting into said cavity and with said pressure cap applying radial inward force onto said velocity transformer, with said velocity transformer deflecting and gripping said guide wire under the influence of said force.

2. An ultrasonic surgical system as claimed in claim 1, wherein said velocity transformer end portion has a plurality of peripherally spaced ribs having radially outer edges which form the radially outer surface in frictional engagement with said pressure cap inner surface.

3. An ultrasonic surgical system as claimed in claim 1, wherein said inner surface of said pressure cap extends from said velocity transformer end portion to enclose a space between said pressure cap inner surface and said velocity transformer thereby to increase the mass of said pressure cap without increasing the diameter thereof.

4. An ultrasonic surgical system as claimed in claim 1, wherein said velocity transformer end portion has a transverse slot extending through the axis and forming opposite resilient sidewall portions for gripping said guide wire inboard end; and said pressure cap has an end wall with a coaxial through hole for extending said guide wire inboard end therethrough.

5. An ultrasonic surgical system as claimed in claim 4, wherein said pressure end cap wall encloses a stress relieving space for relieving the stresses of said guide wire inboard end due to gripping and vibration thereof.

6. An ultrasonic surgical system as claimed in claim 1, wherein said guide wire has an outboard end having a flexible tip portion which is more flexible than the rest of said guide wire outboard end for ease of transverse vibratory movement for entry to restricted passageways of artery lesions.

7. An ultrasonic vascular surgical system comprising:

a generator;

a handpiece connected to said generator;

a transducer mounted on said handpiece and connected to said generator;

a coupling unit connected to said transducer;

a guide wire having an inboard end with said inboard end connected to said coupling unit and with said coupling unit comprising:

a velocity transformer connected to said transducer with said velocity transformer having a transverse groove disposed between resilient groove sidewalls for gripping said guide wire inboard end, and a pressure cap mounted on said velocity transformer in engagement with said groove sidewalls for compressing said groove sidewalls against said guide wire inboard end.

8. An ultrasonic surgical system as claimed in claim 7, wherein said velocity transformer has ends with a plurality of peripherally spaced ribs having radially outer edges which form a radially outer surface in frictional engagement with an inner surface of said pressure cap.

9. An ultrasonic surgical system as claimed in claim 7, wherein said pressure cap encloses a stress relieving space for relieving the stresses of said guide wire inboard end due to gripping and vibration thereof.

10. An ultrasonic surgical system as claimed in claim 7, wherein said guide wire has an outboard end having a flexible tip portion which is more flexible than the rest of said guide wire outboard end for ease of transverse vibratory movement for entry to the restricted passageway of an artery lesion.

* * * * *